United States Patent [19]

Colvin et al.

[11] Patent Number: 4,528,413
[45] Date of Patent: Jul. 9, 1985

[54] PROCESS FOR THE SYNTHESIS AND PURIFICATION OF DIISOPROPENYLBENZENE

[75] Inventors: Howard A. Colvin, Akron; Ronald D. Fiedler, Atwater; Joel Muse, Jr., Kent; Donald E. Smith, Tallmadge, all of Ohio

[73] Assignee: The Goodyear Tire & Rubber Company, Akron, Ohio

[21] Appl. No.: 586,166

[22] Filed: Mar. 5, 1984

[51] Int. Cl.$^3$ ............................................. C07C 5/333
[52] U.S. Cl. .................................. 585/440; 585/254; 585/277; 585/315; 585/321
[58] Field of Search ............... 585/440, 315, 321, 254, 585/277

[56] References Cited

U.S. PATENT DOCUMENTS

| | | | |
|---|---|---|---|
| 2,402,740 | 6/1946 | Doumani et al. | 585/440 |
| 2,443,217 | 6/1948 | Amos et al. | 585/440 |
| 3,100,807 | 8/1963 | Hatfield et al. | 585/440 |
| 3,631,213 | 12/1971 | Brewer | 585/440 |
| 3,652,699 | 3/1972 | Soderquist et al. | 585/440 |
| 4,338,476 | 7/1982 | Vickers et al. | 585/440 |

FOREIGN PATENT DOCUMENTS

| | | | |
|---|---|---|---|
| 20561 | 10/1968 | Australia | 585/440 |
| 43-18767 | 8/1968 | Japan | 585/440 |

Primary Examiner—D. E. Gantz
Assistant Examiner—Cynthia A. Prezlock
Attorney, Agent, or Firm—Alvin T. Rockhill

[57] ABSTRACT

Diisopropenylbenzene is a monomer that can be used in the preparation of many useful polymers and is also a chemical intermediate that can be employed in a number of chemical processes. Diisopropenylbenzene is normally synthesized by the dehydrogenation of diisopropylbenzene. Unfortunately in this dehydrogenation process a number of olefinic impurities are produced as by-products. This invention discloses a process for the separation of diisopropenylbenzene from these impurities and for recycling some of the impurities. In one embodiment of this invention this process comprises: (1) dehydrogenating diisopropylbenzene to form a dehydrogenation mixture containing diisopropenylbenzene and organic impurities, (2) continuously distilling said dehydrogenation mixture to separate said diisopropenylbenzene from said organic impurities, (3) fully hydrogenating said organic impurities to form a mixture of regenerated diisopropylbenzene and saturated organic impurities, and (4) fractionally distilling said mixture of regenerated diisopropylbenzene and saturated organic impurities under conditions sufficient to separate said regenerated diisopropylbenzene from said saturated organic impurities. The regenerated diisopropylbenzene can then be recycled for dehydrogenation with fresh diisopropylbenzene in the first step of the above described process.

12 Claims, 1 Drawing Figure

PROCESS FOR THE SYNTHESIS AND PURIFICATION OF DIISOPROPENYLBENZENE

BACKGROUND OF THE INVENTION

Diisopropenylbenzene is a monomer that can be used in the preparation of many useful polymers and is also a chemical intermediate that can be used in a number of important chemical processes. For example, U.S. Pat. No. 4,403,088 describes plastic resins which are prepared by reacting meta-diisopropenylbenzene or para-diisopropenylbenzene with m-dialkoxybenzenes, 1-mercapto-3-alkoxybenzene, phenol, diaralkoxybenzenes and/or 1,2,3-trialkoxybenzenes. Diisopropenylbenzene can be synthesized by the dehydrogenation of diisopropylbenzene. For example, meta-diisopropylbenzene (m-DIPB) can be dehydrogenated into meta-diisopropenylbenzene (m-DIB) and para-diisopropylbenzene (p-DIPB) can be dehydrogenated into para-diisopropenylbenzene (p-DIB). Unfortunately, in this dehydrogenation process some olefinic impurities are produced as by-products. These olefinic impurities include isopropylstyrene, divinylbenzene, isopropenylstyrene, and other similar organic impurities. Obviously, it would be very desirable to remove these impurities from the meta- or para-diisopropenylbenzene produced by the dehydrogenation of diisopropylbenzene.

Fractional distillation can often be used to remove organic impurities from organic compounds. However, attempts to remove these organic impurities from p-DIB and m-DIB by batch fractional distillation have resulted in the contents of the distillation pot (p-DIB or m-DIB and the organic impurities) polymerizing into a gel at the elevated temperature needed for the the distillation making it impossible. This polymerization even takes place with as much as 1,000 ppm (parts per million) of polymerization inhibitor present in the distillation pot with gel formation occurring long before all of the diisopropenylbenzene can be recovered.

Sometimes unwanted by-products can be removed by hydrogenation. For example, U.S. Pat. Nos. 3,887,632, 3,912,789, and 3,922,318 show that acetylenes can be removed from a stream containing butadiene and/or isoprene by selective hydrogenation.

SUMMARY OF THE INVENTION

It has been unexpectedly found that a dehydrogenation mixture (mixture of diisopropenylbenzene and organic impurities formed in the dehydrogenation of diisopropylbenzene) can be fractionally distilled in a continuous distillation process to separate the m-DIB or p-DIB from the organic impurities without gel formation, even though such a separation cannot be done using a batch distillation process without causing the contents of the distillation pot to polymerize into a gel. Thus, this invention reveals a process for the separation of diisopropenylbenzene from organic impurities by using a continuous distillation process. It also discloses a process for recycling some of the organic impurities produced in the dehydrogenation of diisopropylbenzene which are separated from the diisopropenylbenzene in the continuous distillation process.

This invention discloses a process for the synthesis of diisopropenylbenzene which comprises: (1) dehydrogenating diisopropylbenzene to form a dehydrogenation mixture containing diisopropenylbenzene and organic impurities, (2) continuously distilling said dehydrogenation mixture to separate said diisopropenylbenzene from said organic impurities, (3) fully hydrogenating said organic impurities to form a mixture of regenerated diisopropylbenzene and saturated organic impurities, and (4) fractionally distilling said mixture of regenerated diisopropylbenzene and saturated organic impurities under conditions sufficient to separate said regenerated diisopropylbenzene from said saturated organic impurities. The regenerated diisopropylbenzene can then be recycled for dehydrogenation with fresh diisopropylbenzene in the first step of the process.

This invention also reveals a process for the synthesis of diisopropenylbenzene which comprises: (1) dehydrogenating diisopropylbenzene to form a dehydrogenation mixture containing diisopropenylbenzene, isopropenylstyrene, isopropylisopropenylbenzene, and other organic impurities, (2) continuously distilling said dehydrogenation mixture to separate said diisopropenylbenzene from a mixture of said isopropenyl styrene, said isopropylisopropenylbenzene and the other organic impurities, (3) selectively hydrogenating said isopropenylstyrene in said mixture of said isopropenylstyrene, said isopropylisopropenylbenzene and the other organic impurities to a maximum residual isopropenylstyrene concentration of no more than about 7 percent by weight in the presence of a rhodium catalyst and hydrogen to form a partially hydrogenated dehydrogenation mixture, and (4) fractionally distilling said partially hydrogenated dehydrogenation mixture under conditions sufficient to separate said isopropylisopropenylbenzene and the residual isopropenylstyrene from the other organic impurities. The mixture of isopropylisopropenylbenzene and residual isopropenylstyrene recovered by this process can be recycled for dehydrogenation to diisopropenylbenzene in the first step of this process. It does not need to be fully hydrogenated in order to be recycled.

This invention further discloses a process for the separation of diisopropenylbenzene from organic impurities in a dehydrogenation mixture comprising continuously distilling said dehydrogenation mixture in a continuous recovery column to separate said diisopropenylbenzene from said organic impurities.

DETAILED DESCRIPTION

Figure 1:
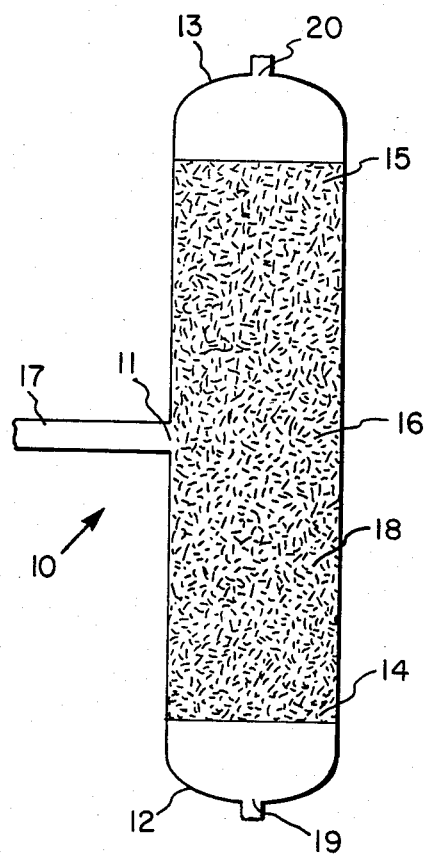

Meta-diisopropenylbenzene and para-diisopropenylbenzene can be produced by the dehydrogenation of meta-diisopropylbenzene and para-diisopropylbenzene, respectively. Such dehydrogenations are generally done in the presence of iron oxide catalysts. In this diisopropylbenzene dehydrogenation process a dehydrogenation mixture is produced that contains diisopropenylbenzene and a number of organic impurities. These organic impurities include isopropylstyrene, divinylbenzene, isopropenylstyrene, isopropylisopropenylbenzene, and a number of other olefinic impurities. A small amount of diisopropylbenzene that was not dehydrogenated is usually also present in the dehydrogenation mixture. During the dehydrogenation of meta-diisopropylbenzene as much as 12 percent of the dehydrogenation mixture produced can be isopropenylstyrene which is produced as an unwanted by-product. Large amounts of isopropylisopropenylbenzene (ENE) can also be present in such dehydrogenation mixtures.

Such dehydrogenation mixtures can be continuously distilled so as to separate the diisopropenylbenzene (DIB) from the organic impurities which are present.

FIG. 1 depicts a continuous recovery column useful for the continuous distillation of the dehydrogeneration effluent to separate the organic impurities contained therein.

This type of continuous distillation can be done in a continuous recovery column. Such a continuous recovery column 10 is shown in diagrammatic form in FIG. 1. The dehydrogenation mixture is introduced into the continuous recovery column through a feed port 11 which is generally in the midsection 16 of the continuous recovery column. The midsection of the continuous recovery column is the area in the middle one-third of the continuous recovery column as measured from the bottom 12 of the column to the top 13 of the column. Thus, the feed port will not normally be located in the lower portion 14 (lower one-third) or the upper portion 15 (upper one-third) of the continuous recovery column 10. The dehydrogenation mixture will generally be pumped through a feed line 17 to the feed port 11 and then into the continuous recovery column.

Such a continuous recovery column can be packed or can be of the tray type. In order to increase the number of theoretical plates in the continuous recovery column it is preferable for it to be packed. It can, for example, be packed with conical or cylindrical helices 18 which are preferably made of copper or stainless steel. Stainless steel Pall rings can also be used as packing for the continuous recovery column. A high efficiency dumped packing is most preferred for use in the continuous recovery column.

The continuous recovery column should be designed in such a way that the temperature gradient along its length is minimized (from the top of the column to the bottom of the column). The packing at the bottom of the continuous recovery column will generally have a temperature in the range of about 130° C. to about 150° C. and the temperature at the top of the continuous recovery column will normally have a temperature in the range of from about 75° C. to about 95° C. The temperature of the packing in the midsection of the continuous recovery column will generally be in the range of about 100° C. to about 125° C. Typically the continuous distillation will be run at an absolute pressure of 10 to 15 mm of mercury or under an even greater amount of vacuum. A dehydrogenation mixture can be fed into the continuous recovery column without preheating, however, it is generally preferred for the dehydrogenation mixture to be preheated to a temperature between about 50° C. and about 100° C. and more preferred for it to be preheated to a temperature from 70° C. to 90° C. Purified DIB is recovered through the bottom recovery port 19 at the bottom of the continuous recovery column and a mixture of organic impurities including ENE, DIPB, and isopropenylstyrene (IPS) are recovered through the top recovery port 20 at the top of the column. Persons skilled in the art will realize that the continuous recovery column described herein can be modified in various ways and will be able to ascertain the specific temperatures, pressures and conditions needed for its most efficient operation.

Large quantities of organic impurities are recovered as the overhead fraction, through the top recovery port, and it is important that they be utilized in some manner. Since a large amount of ENE is present in this mixture of organic impurities it would be very desirable to recycle it to be dehydrogenated with fresh DIPB. However, in order for the ENE to be recycled the IPS present in the mixture of organic impurities must first be removed. This is because the presence of IPS, even in low concentrations, will cause fouling of the preheater to the dehydrogenation reactor (probably due to polymerization of the IPS). Ideally, the IPS could be separated from such mixtures of organic impurities by fractional distillation. However, the boiling points of ENE and IPS are almost identical which makes their separation by fractional distillation very impractical. The tendency of IPS to polymerize to a gel during distillation is another problem that makes such a fractional distillation almost impossible.

In the practice of this invention, in order to make recycle possible, mixtures of organic impurities which contain IPS are hydrogenated so as to remove the IPS from the mixture of organic impurities. Such mixtures can be fully hydrogenated so as to form a mixture of saturated organic impurities with the ENE in the mixture being hydrogenated into regenerated diisopropylbenzene. This process of fully hydrogenating the organic impurities to form a mixture of regenerated DIPB and saturated organic impurities results in essentially all of the non-aromatic carbon-carbon double bonds in the unsaturated organic impurities being converted into carbon-carbon single bonds. Thus the IPS in the mixture is converted into ethylisopropylbenzene. Such a full hydrogenation can be done using hydrogenation techniques well known to those skilled in the art.

The IPS in such mixtures of IPS, ENE, and other organic impurities can also be removed by selectively hydrogenating the IPS. If a selective hydrogenation of IPS is utilized it is important that the concentration of IPS in the partially dehydrogenated hydrogenation mixture be reduced to no more than about 7 percent by weight. Greater amounts of IPS can cause fouling of the preheater to the dehydrogenation reactor when recycled with fresh DIPB in normal quantities. It is more preferred for the amount of IPS present to be reduced to no more than about 4 weight percent. One advantage to such a selective hydrogenation is that a partially hydrogenated dehydrogenation mixture is formed wherein the ENE is not hydrogenated back to DIPB. Thus, upon recycle only one isopropyl group on the ENE needs to be dehydrogenated in order to convert it into DIB. If the ENE is hydrogenated back to DIPB then two isopropyl groups need to be dehydrogenated in order to convert it into DIB. In other words, the selective hydrogenation process is more efficient in this respect.

It has been found that IPS can be removed from mixtures of unsaturated organic impurities by selective hydrogenation utilizing a rhodium catalyst. The rhodium catalyst that is used in this selective dehydrogenation reaction can be either supported or unsupported. It is generally preferable for the rhodium to be supported. Some representative examples of supports that can be used for the rhodium include: carbon, aluminum oxide (alumina), barium sulfate, calcium carbonate, and strontium carbonate. A rhodium-on-charcoal catalyst is an excellent choice as the catalyst in this hydrogenation reaction. The catalyst can be in a fixed bed for hydrogenation on a continuous basis or distributed throughout the dehydrogenation mixture in the case of a batch process. This hydrogenation of the dehydrogenation mixture obviously must be conducted in the presence of hydrogen gas.

This selective hydrogenation reaction can be done in a batch process by distributing the hydrogen gas and rhodium catalyst throughout the dehydrogenation mixture. For example, hydrogen gas can be sparged through the dehydrogenation mixture containing the catalyst while agitating the dehydrogenation mixture to keep the catalyst well dispersed throughout the mixture. This selective hydrogenation reaction can be run on a continuous basis by introducing hydrogen gas into the zone of the fixed bed catalyst while passing the dehydrogenation mixture through the fixed bed catalyst.

This selective hydrogenation reaction can be carried out at atmospheric pressure ($1.0 \times 10^5$ Pa) up to about 1000 gauge pounds per square inch ($7.0 \times 10^6$ Pa). It is preferred for the hydrogenation reaction to be run at about 50 gauge pounds per square inch ($4.5 \times 10^5$ Pa) up to about 70 gauge pounds per square inch ($5.8 \times 10^5$ Pa).

The selective hydrogenation of IPS can be run at a temperature from about 0° C. up to about 120° C. Such a selective hydrogenation reaction should preferably be continued until about 2 moles of hydrogen are absorbed for every mole of isopropenylstyrene originally present in the mixture of unsaturated organic impurities. More preferably the hydrogenation should be continued until 3 moles of hydrogen are absorbed for every mole of isopropenylstyrene originally present. The selective hydrogenation of mixtures of unsaturated organic impurities results in formation of partially hydrogenated dehydrogenation mixtures.

The rhodium catalyst can be removed from a partially hydrogenated dehydrogenation mixture that was hydrogenated in a batch process by filtration, centrifugation, sedimentation, and the like. If a fixed bed catalyst is used in a continuous hydrogenation process then obviously there is no catalyst that needs to be removed from the hydrogenated dehydrogenation mixture.

Mixtures of regenerated DIPB and saturated organic impurities, as well as partially hydrogenated dehydrogenation mixtures, can be fractionally distilled using distillation techniques well known to those skilled in the art to recover DIPB and/or ENE. A batch distillation process or a continuous distillation process can be used. The DIPB or ENE which is recovered can then be recycled with fresh DIPB for dehydrogenation into DIB.

The following examples are merely for the purpose of illustration and are not to be regarded as limiting the scope of the invention or the manner in which it can be practiced. Unless specifically indicated otherwise parts and percentages are given by weight.

EXAMPLE 1

Meta-DIPB feed was charged into a dehydrogenation reactor at a rate of about 9 pounds per hour (lbs/hr). The dehydrogenation mixture produced exited the dehydrogenation reactor as a stream containing 0.5 lbs/hr of m-DIPB, 0.4 lbs/hr of m-IPS, 1.0 lbs/hr of isopropylisopropenylbenzene(m-isopropenyl cumene), and 5.2 lbs/hr of m-DIB.

A stream of this dehydrogenation mixture was then fed into a continuous recovery column at a rate of 14.5 lbs/hr. This stream was fed into the continuous recovery column at a temperature of about 80° C. through a feed port located 9 feet above the bottom of the column. This continuous recovery column contained 24 feet of packing and was operated at a pressure of 15 millimeters of mercury. The continuous recovery column was operated with a reboiler temperature of 150° C. and had a temperature profile as measured at various distances from the bottom of the column as follows:

| Distance from bottom | Temperature |
|---|---|
| 0 feet | 144.3° C. |
| 5 feet | 128.4° C. |
| 9 feet | 124.5° C. |
| 17 feet | 110.4° C. |
| 22 feet | 87.2° C. |
| 26 feet | 82.2° C. |

Meta-DIB was recovered through the bottom recovery port at a rate of 9.0 lbs/hr. The stream recovered through the top recovery port contained 0.9 lbs/hr of m-DIPB, 1.7 lbs/hr of isopropylisopropenylbenzene, 0.6 lbs/hr of isopropenylstyrene and 0.04 lbs/hr of m-DIB. This stream could then be hydrogenated over a supported noble metal so as to fully hydrogenate all of the olefinic compounds in the stream.

This fully hydrogenated stream could then be fractionally distilled in a continuous process to regenerated m-DIPB. This regenerated m-DIPB could then be recycled with fresh m-DIPB for dehydrogenation in the dehydrogenation reactor.

EXAMPLE 2

Meta-diisopropylbenzene was dehydrogenated to a crude dehydrogenation mixture that contained the composition shown in Table I. 194 g (grams) of this dehydrogenation mixture was placed into a Parr bottle with 0.6 g of 5% rhodium-on-charcoal catalyst (50% water weight). The catalyst added contained only 0.015 g of rhodium (50% of the 0.6 g was water weight and 95% of the remaining 0.3 g was carbon). This dehydrogenation mixture was hydrogenated with 50 gauge pounds per square inch ($4.5 \times 10^5$ pa) of hydrogen gas at room temperature. The composition of the hydrogenated dehydrogenation mixture being produced was determined after 1, 2, and 3 moles of hydrogen per mole of isopropenylstyrene originally present in the dehydrogenation mixture was absorbed. The amounts of the various components given in Table I are given as area percentages as determined by gas chromatography.

TABLE I

| IPS Component | Gas Chromatograph Area Percentages for Various Mixture Components | | | |
|---|---|---|---|---|
| | Moles of $H_2$ absorbed/mole | | | |
| | 0 | 1 | 2 | 3 |
| m-isopropenylethylbenzene | 2.0 | 4.1 | 6.3 | 8.5 |
| m-diisopropylbenzene | 8.7 | 9.1 | 9.2 | 9.8 |
| m-isopropenylstyrene | 7.5 | 5.4 | 2.8 | 0.3 |
| m-isopropenylisopropylbenzene | 16.5 | 16.1 | 15.8 | 16.1 |
| m-diisopropenylbenzene | 39.8 | 38.6 | 39.0 | 37.8 |

As can be determined from Table I, after 2 moles of hydrogen per mole of IPS had been absorbed 63 percent of the m-IPS was removed (hydrogenated) while only 4 percent of the ENE was removed. After 3 moles of hydrogen per mole of IPS had been absorbed 96% of the m-IPS was removed while only 2% of the ENE was removed. This example illustrates the fact that rhodium is an excellent catalyst for the selective hydrogenation of IPS which hydrogenates only a minimal amount of ENE. Rhodium catalysts have a unique ability to selectively hydrogenate IPS and thus are used in the selective hydrogenations of this invention.

While certain representative embodiments and details have been shown for the purpose of illustrating the invention, it will be apparent to those skilled in this art that various changes and modifications may be made therein without departing from the scope of the invention.

What is claimed is:

1. A process for the synthesis and purification of diisopropenylbenzene from diisopropylbenzene and regenerated diisopropylbenzene which comprises: (1) dehydrogenating diisopropylbenzene to form a dehydrogenation mixture containing diisopropenylbenzene and organic impurities including a number of olefinic impurities, (2) continuously distilling said dehydrogenation mixture to separate said diisopropenylbenzene from said organic impurities, (3) fully hydrogenating said organic impurities to form a mixture of regenerated diisopropylbenzene and saturated organic impurities, (4) fractionally distilling said mixture of regenerated diisopropylbenzene and saturated organic impurities under conditions sufficient to separate said regenerated diisopropylbenzene from said saturated organic impurities, and (5) recycling said regenerated diisopropylbenzene to the first step of this process for dehydrogenation.

2. A process as specified in claim 1 wherein said diisopropenylbenzene is meta-diisopropenylbenzene and wherein said diisopropylbenzene is meta-diisopropylbenzene.

3. A process as specified in claim 1 wherein said diisopropenylbenzene is para-diisopropenylbenzene and wherein said diisopropylbenzene is para-diisopropylbenzene.

4. A process as specified in claim 2 wherein said continuous distilling is conducted in a continuous recovery column.

5. A process as specified in claim 3 wherein said continuous distilling is conducted in a continuous recovery column.

6. A process for the synthesis and purification of diisopropenylbenzene from a mixture of diisopropylbenzene and isopropylisopropenylbenzene which comprises: (1) dehydrogenating said mixture of said diisopropylbenzene and said isopropylisopropenylbenzene to form a dehydrogenation mixture containing diisopropenylbenzene, isopropenyl styrene, isopropylisopropenylbenzene, and other organic impurities, (2) continuously distilling said dehydrogenation mixture to separate said diisopropenylbenzene from a mixture of said isopropenyl styrene, said isopropylisopropenylbenzene and the other organic impurities, (3) selectively hydrogenating said isopropenylstyrene in said mixture of said isopropenyl styrene, said isopropylisopropenylbenzene and the other organic impurities to a maximum residual isopropenylstyrene concentration of no more than about 7 percent by weight in the presence of a rhodium catalyst and hydrogen to form a partially hydrogenated dehydrogenation mixture, (4) fractionally distilling said partially hydrogenated dehydrogenation mixture under conditions sufficient to separate a mixture of said isopropylisopropenylbenzene and the residual isopropenylstyrene from the other organic impurities, and (5) recycling said mixture of said isopropylisopropenylbenzene and said residual isopropenylstyrene to the first step of this process for dehydrogenation.

7. A process as specified in claim 6 wherein said diisopropenylbenzene is meta-diisopropenylbenzene and wherein said diisopropylbenzene is meta-diisopropylbenzene.

8. A process as specified in claim 6 wherein said diisopropenylbenzene is para-diisopropenylbenzene and wherein said diisopropylbenzene is para-diisopropylbenzene.

9. A process as specified in claim 6 wherein selective hydrogenation is done at a temperature of from about 0° C. up to about 120° C. and a pressure of about $1.0 \times 10^5$ Pa up to about $7.0 \times 10^6$ Pa.

10. A process as specified in claim 9 wherein said rhodium catalyst is supported.

11. A process as specified in claim 10 wherein said rhodium catalyst is supported with a member selected from the group consisting of carbon, aluminum oxide, barium sulfate, calcium carbonate, and strontium carbonate.

12. A process as specified in claim 6 wherein said isopropenylstyrene in said mixture of said isopropenylstyrene, said isopropylisopropenylbenzene and the other organic impurities is selectively hydrogenated to a concentration of no more than about 4 weight percent in said partially hydrogenated dehydrogenation mixture.

* * * * *